(12) United States Patent
Bello

(10) Patent No.: US 7,728,291 B2
(45) Date of Patent: Jun. 1, 2010

(54) DETECTION OF HEAVY OIL USING FLUORESCENCE POLARIZATION

(75) Inventor: Job M. Bello, Swansea, MA (US)

(73) Assignee: EIC Laboratories, Inc., Norwood, MA (US)

( * ) Notice: Subject to any disclaimer, the term of this patent is extended or adjusted under 35 U.S.C. 154(b) by 0 days.

(21) Appl. No.: 12/321,433

(22) Filed: Jan. 21, 2009

(65) Prior Publication Data

US 2009/0189074 A1 Jul. 30, 2009

Related U.S. Application Data

(60) Provisional application No. 61/024,337, filed on Jan. 29, 2008.

(51) Int. Cl.
*G01T 1/169* (2006.01)
(52) U.S. Cl. .................................... 250/301; 250/484.2
(58) Field of Classification Search ................. 250/301, 250/484.2
See application file for complete search history.

(56) References Cited

U.S. PATENT DOCUMENTS

| | | | |
|---|---|---|---|
| 5,065,019 A | 11/1991 | Darilek et al. |
| 5,604,582 A | 2/1997 | Rhoads et al. |
| 5,974,860 A | 11/1999 | Kuroda et al. |
| 6,563,122 B1 | 5/2003 | Ludeker et al. |
| 6,633,043 B2 | 10/2003 | Hegazi et al. |
| 6,704,109 B2 | 3/2004 | Wu et al. |
| 7,009,550 B2 | 3/2006 | Moeller-Jensen et al. |
| 7,227,139 B2 | 6/2007 | Kram et al. |

2002/0070349 A1 * 6/2002 Hoyt ........................ 250/458.1

OTHER PUBLICATIONS

Reuter et al, A Laser Fluorosensor for Maritime Surveillance: Measurement of Oil Spills, EARScL Advances in Remote Sending, vol. 3, No. 3-VII, 1995, pp. 152-169.

Chase et al, Advanced Detection Technology for Early Warning—The Key to Oil Spill Prevention, For Presentation at International Oil Spill Conference, May 2008, 15 pages.

P.A. Tebeau et al, Cost-Benefit Analysis for Using Laser Fluorosensor for Detecting Heavy Oil, U.S. Coast Guard Research and Development Center, Report No. CG-D-01-07, Nov. 2006, 108 pages.

Ko et al, Early dental caries detection using a fibre-optic coupled polarization-resolved Raman spectroscopic system, vol. 16, No. 9, Optics Express, Apr. 28, 2008, pp. 6274-6284.

Schultze et al, Laser-induced fluorescence (LIF) spectroscopy for the in situ analysis of petroleum product-contaminated soils, Universitat Potsdam, 2004, 21 pages.

Schade et al, On-Site Laser Probe for the Detection of Petroleum Products in Water and Soil, Environ. Sci. Technol., 1996, 1451-1458.

(Continued)

*Primary Examiner*—David P Porta
*Assistant Examiner*—Mark R Gaworecki
(74) *Attorney, Agent, or Firm*—Goodwin Procter LLP

(57) ABSTRACT

Viscous oil residues are located based on fluorescence polarization. Methods and apparatus in accordance with the invention may be integrated with autonomous and remotely operated undersea vehicles to map the location of oil spills.

17 Claims, 7 Drawing Sheets

OTHER PUBLICATIONS

Raman Polarization Accessory for the RamanStation 400, PerkinElmer, 2008, 4 pages.

Thomson et al, Raman spectroscopy with simultaneous measurement of two orthogonally polarized Raman spectra, J. Raman Spectrosc. 2003, 345-349.

GE, Leakwise Oil-on-Water Detection and Monitoring Systems, GE Water & Process Technologies Analytical Instruments, www.geinstruments.com 2005, 6 pages.

Harsdorf et al, Submarine lidar for searfloor inspection, Meas. Sci. Technol. 10 (1999) 1178-1184.

* cited by examiner

DETECTION OF HEAVY OIL USING FLUORESCENCE POLARIZATION

RELATED APPLICATION

This application claims priority to, and the benefits of, U.S. Provisional Application Ser. No. 61/024,337, filed on Jan. 29, 2008, the entire disclosure of which is hereby incorporated by reference.

GOVERNMENT RIGHTS

This invention was made with Government support under Contract No. HSCG32-07-C-R00013 awarded by the U.S. Coast Guard Research and Development Center. The Government has certain rights to this invention.

FIELD OF INVENTION

This invention relates to devices and methods for detecting the composition and location of viscous oil residues such as oil spills or oil deposits in subsurface locations, particularly on the floor of oceans, lakes and other aquifers.

BACKGROUND OF INVENTION

Increased consumption and transportation of oil and its products exacerbate the problem of pollution in lakes and oceans. Even with strict regulation of oil transportation, accidents leading to oil spills still occur frequently. Indeed, numerous accidents occur annually, with thousands of tons of oil being spilled into seas, contaminating marine environments and endangering marine ecology. Of the oil that is spilled, a significant fraction of the residual oil is heavier than water and sinks to the bottom; this oil fraction is frequently termed Group V oils, which have a specific gravity exceeding 1.0. These oil residues are typically rich in polynuclear aromatic hydrocarbons (PAHs), which are toxic to aquatic life. Oil spills in coastal waters, harbors, and oil terminals are especially dangerous and necessitate a rapid response when they occur in order to prevent contamination of marine habitats. Therefore, reliable oil-spill detection systems which can locate and map subsurface spillage are needed.

A number of known methods for detecting oil spills are mostly limited to surface oil. It is well known that oils contain fluorophores, i.e., molecules and functional groups that exhibit fluorescence when excited by light of a wavelength absorbed by such moieties. For example, remote laser-induced fluorescence has been developed for surface oil detection. Airborne fluorescence LIDAR (laser-induced detection and ranging), which combines fluorescence detection with ranging techniques, has been developed as well. However, airborne fluorescence methods are generally unable to detect deep underwater oil contaminants. Furthermore, fluorescence methods are susceptible to interference from other fluorophores in water, such as humic compounds, chlorophyll and other plant pigments.

Methods for subsurface detection and mapping of heavy oils include visual observation, cameras and acoustic/sonar sounding methods. Because of the similarity in oil and other natural sediments, these methods, while providing a rapid survey, generally require confirmation by further sampling and analysis, and therefore do not offer real-time results. Sonar frequently does not provide sufficient contrast with the sedimentary sea floor.

Therefore, there is a need for economical methods and instruments to can detect and image heavy-oil residues in real-time with minimal interferences.

SUMMARY OF THE INVENTION

Embodiments of the present invention provide methods and instruments for detecting heavy oil spills based on fluorescence in a manner free of interferences from non-oil fluorescing media (e.g., chlorophylls and the daylight background). Instruments in accordance with the invention may be deployed remotely for scanning and monitoring the floor of waterways, lakes and oceans.

In various embodiments, the present invention employs fluorescence polarization (FP) to differentiate heavy or viscous oil from other fluorophores, e.g., vegetation, organic matter or light petroleum chemicals such as gasoline. Thus, the present invention may be advantageously employed in detecting the presence of heavy oil (densities exceeding 1 g/cm$^3$) that sinks in water. In addition, some high-viscosity oils have densities less than 1 g/cm$^3$, forming surface oil slicks that also display FP and, consequently, can be detected in accordance herewith.

FP can be considered a competition between the molecular motion and the lifetime of the fluorescing excited state of a fluorophore. If an ensemble of fluorophores is exposed to linearly polarized light, only those fluorophores aligned with the plane of polarization will be excited. The amount of polarization retained in the emitted fluorescence will depend on how much the molecule has rotated during the lifetime of the excited fluorescing state. Thus, the fluorescence polarization depends on the fluorescence lifetime and the rotational correlation time ($\theta$). The rotational correlation time is given by $\theta=\eta V/kT$, where k is the Boltzman constant, T is the absolute temperature, $\eta$ is the viscosity and V is the molecular volume. Thus, viscous samples favor fluorescence polarization. In particular, heavy oils, which are very viscous, show significant fluorescence polarization when excited with polarized light while typical interfering fluorophores do not.

In a typical measurement employed herein, the fluorescent sample is excited with linear polarized light at a wavelength that overlaps the sample's absorption spectrum, and the intensities of the vertically and horizontally polarized emitted light are determined. The polarization (P) or anisotropy (r) are calculated using the following equations:

Polarization $(P)=(I_v-I_h)/(I_v+I_h)$

Anisotropy $(r)=(I_v-I_h)/(I_v+2I_h)$ where $I_v$ is the emission intensity parallel to the excitation plane and $I_h$ is the emission intensity perpendicular to the excitation plane. Viscous fluorescing residues will feature elevated values of P and r. Nonviscous samples will tend to exhibit small or null values of P and r, since $(I_v-I_h)$ will approach zero.

Accordingly, in a first aspect, embodiments of the invention pertain to apparatus for detecting the presence of oil in an aqueous environment. An apparatus in accordance with the invention may include a source of polarized fluorescence excitation light; a collector for collecting fluorescence from a target region to which the source is directed; a separator for separating vertically and horizontally polarized components of the collected fluorescence; and an analysis module for determining the presence of oil based on intensities of the vertically and horizontally polarized components.

In some embodiments, the intensities of the vertically and horizontally polarized components are measured with an optical detector. The detector may include one or more optical filters to separate the collected fluorescence from the excitation light. In some embodiments, the detector includes means for recording the intensities of the vertically and horizontally polarized components as spectra. The apparatus may also include a light shield for preventing interference from ambient sunlight. It may further employ spectrographs to record the fluorescence spectra, and these may provide further information on the composition(s) of the fluorophores.

Instruments in accordance with the invention may be deployed to scan the floor of the ocean or other waterway. For example, the source and collector may be physically separate from, but communicate with, the separator and the analysis module. In some embodiments, the optical components are tethered to the active components using fiber-optic cable. The optical components may then be dropped from a vessel. In other embodiments, the optical components communicate wirelessly with the active components. In still other embodiments, the instrument is self-contained in a sealed enclosure, which may also be dropped from a vessel or carried by a diver. The instrument may be deployed in an autonomous underwater vehicle (AUV) or a tethered remotely operated vehicle (ROV) with an optical port for scanning the underwater terrain. Instruments in accordance with the invention may also be operated in combination with a wide-area scanning device, such as sonar, to first detect areas of suspicion, which are then analyzed to confirm heavy oil contamination. For ranging, fluorescence polarization may be combined with fluorescence LIDAR in order to provide mapping of distance of viscous fluorophores from the excitation source.

In various embodiments, an apparatus in accordance with the invention includes an imaging module for providing an image of detected oil and/or a mapping module for providing a geographic map of detected oil.

In a second aspect, embodiments of the invention relate to a method of detecting the presence of oil in an aqueous environment. A method in accordance with the invention may include the steps of directing polarized fluorescence excitation light at a target region; collecting fluorescence from the target region; separating vertically and horizontally polarized components of the collected fluorescence; and determining the presence of oil based on intensities of the vertically and horizontally polarized components.

In some embodiments, the method further comprises measuring the intensities of the vertically and horizontally polarized components. The method may include separating the collected fluorescence from the excitation light and/or the step of recording the intensities of the vertically and horizontally polarized components as spectra. In some embodiments, interference from ambient sunlight is prevented.

It may be desirable to generate an image and/or a geographic map of detected oil. In some embodiments, a wide area is scanned to identify an area of suspicion corresponding to the target region.

Apparatus and methods in accordance herewith may be modified to sense or monitor for surface oil slicks of viscous oils such as might arise in aquifers surrounding oil refineries, shipyards, airports and military bases. A typical configuration entails mounting the optical components above the aquifer surface to detect polarized fluorescence on the surface region. An instrument deployed in this fashion may use a continuous light source, unlike fluorescence-based oil-slick monitors which typically employ pulsed light sources and time gating to reject ambient light.

DETAILED DESCRIPTION

Figure 1:
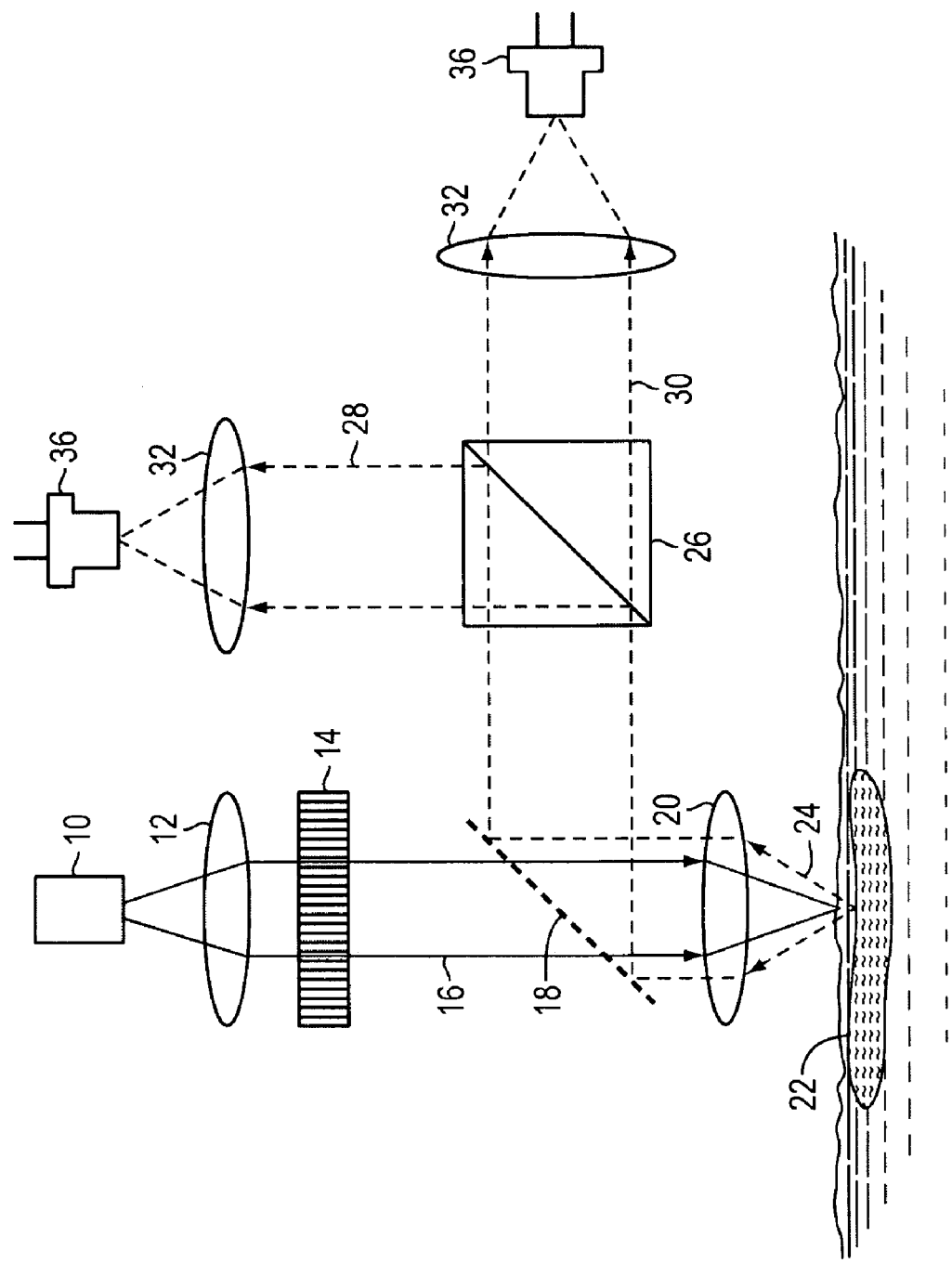
FIG. 1 schematically illustrates a fluorescence polarization instrument for examining subsurface aquifer residues.

A representative apparatus in accordance with the invention is illustrated schematically in FIG. 1. A light source 10, typically a laser, is used to excite fluorescence in the location under study. The diverging source is passed through a collimating lens or lens assembly 12, then through a polarizer 14. The emerging polarized light 16 is then passed through a dichroic mirror or beamsplitter 18, typically set at 45° to the light path. The dichroic element 18 passes the exciting laser frequency and reflects lower frequencies. The polarized light beam is focused by a lens or lens assembly 20 onto the region under study containing the heavy oil 22. The characteristics of the lens 20, or similar focusing combination of lens and/or mirror elements, set the focal distance. A mechanically adjustable lens array may be used to provide a variable focus. In the configuration shown in FIG. 1, fluorescence 24 is collected in a 180° backscattering mode, a configuration that desirably reduces the number of optical elements relative to configurations having separate excitation and collection optical assemblies. This fluorescence 24 contains both vertically and horizontally polarized components that arise due to rotation of the fluorophores in the interval between excitation and emission, as explained above. The collected fluorescence retraces, in reverse, the optical path of the excitation beam and is then reflected at 45° off the dichroic mirror 18. The reflected light is directed to an optical element for separating polarization components. This may take the form of a polarizing cube beamsplitter 26, which separates the vertically and horizontally polarized components 28, 30 of the fluorescence, directing them at 90° and 180°, respectively, to the incoming light path. The resulting beams are focused by lenses 32 onto separate photodetectors (e.g., photodiodes) 36, where the ratio of their intensities may be determined, and hence the polarization and anisotropy values calculated. The polarized components may first traverse filters that selectively pass fluorescence wavelengths and reject any spurious wavelengths, thereby reducing interferences.

Figure 2B:
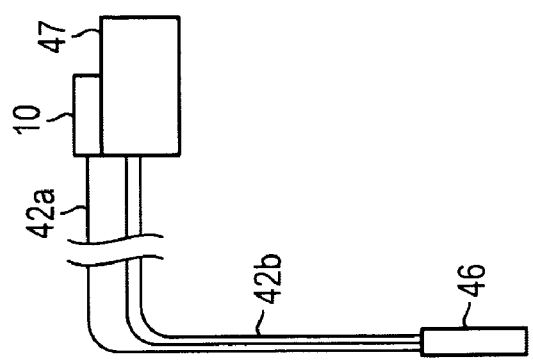
FIGS. 2A and 2B schematically illustrate a confocal fluorescence polarization probe with fiber-optic coupling.
Figure 2A:
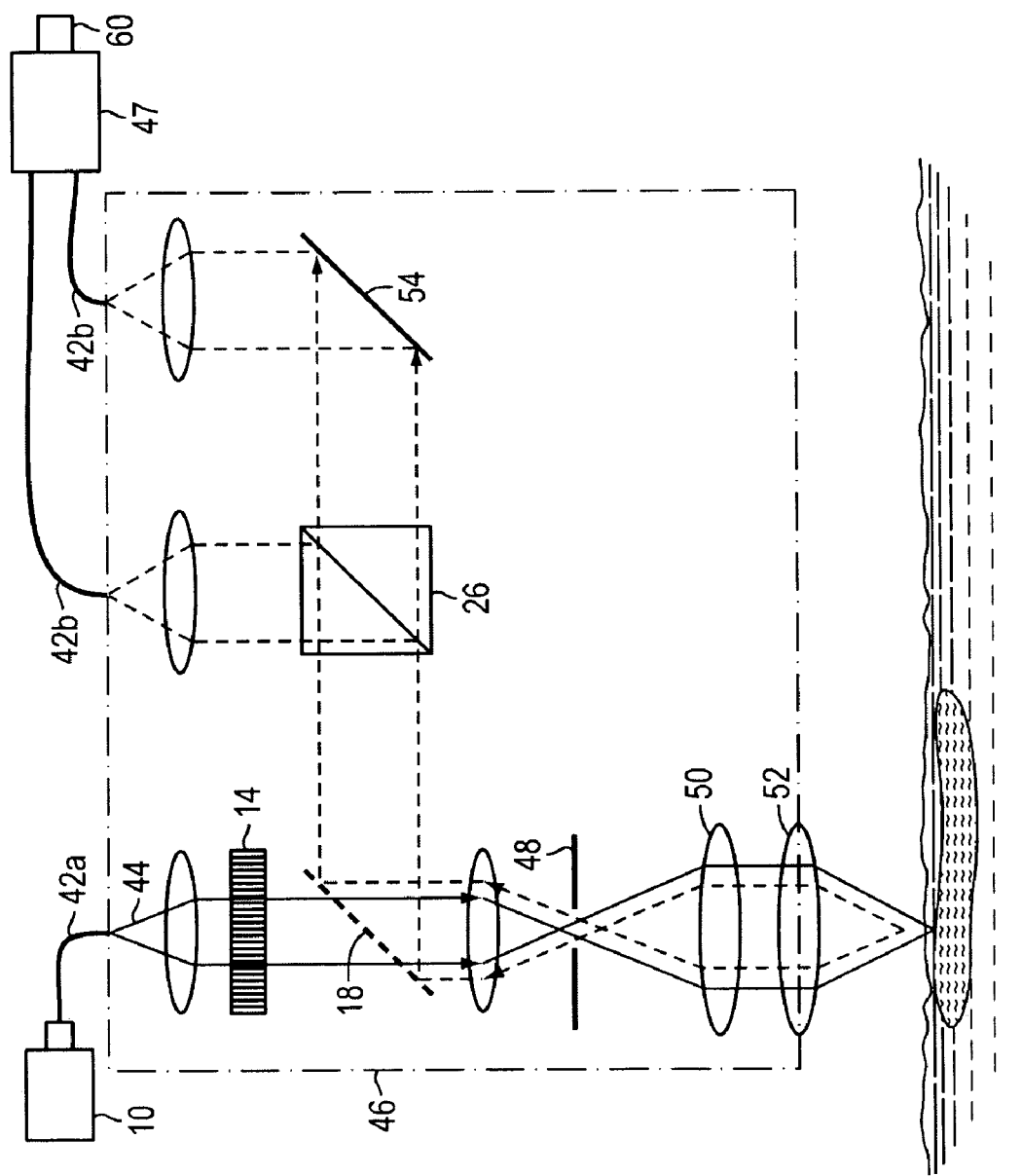

In the deployment shown in FIG. 2, the fluorescence polarization components are coupled to active optical and electro-optical elements (the excitation laser and detection system) by optical fibers. Such an arrangement is useful when the measurements are to be made in a confined or hostile environment, or when larger or more complex laser and/or detection equipment is used and is most easily confined to a surface facility. The illustrated probe also incorporates a spatial filtering feature that reduces background noise caused by daylight, and therefore makes the apparatus useful in both day and night operations. Finally, the photodiode detectors are replaced by remotely situated spectrographs that can measure the spectral distribution of the polarized light components and therefore provide information about the nature of the fluorescing species by comparing the spectra to a database of known fluorophores.

With reference to FIG. 2, the excitation source 10 is coupled to an optical fiber fiber optic 42a, the expanding output 44 of which enters the optical assembly via collimating lens 12. The entire optical assembly in this configuration is enclosed in a probe housing 46, which is remotely connected via optical fiber links 42a, 42b to the laser 10 and a spectrograph 47. Light passes through the polarizer and dichroic beamsplitter as in FIG. 1. A potential source of interference is the ambient light background. This may be eliminated to a large degree by introducing a spatial filter 48 comprising a small hole ("pinhole") into the excitation and collection optical path. Thus, the optical assembly only images light originating from an in-focus plane, which freely passes through the pinhole. Light (such as solar background radiation) coming from out-of-focus planes is largely blocked by the pinhole. Light exiting the spatial filter is recollimated by lens element 50 and, optionally, focused onto the region under study by lens 52. (In order to provide a larger area of interrogation, the focusing lens 52 may be eliminated at the possible expense of a somewhat weaker return signal.) The backscattered fluorescence is collected along the same optical path, reflected by the dichroic filter and passed through the polarizing element as in FIG. 1. In order to provide a co-linear probe arrangement, the 180° transmitted component is redirected by 90° with a 45° mirror 54. The fluorescence components are focused into optical fibers 42b, which are directed to separate spectrographs, or two channels of a single spectrograph 47. The spectrograph(s), with a suitable detector 60 such as a charge-coupled device (CCD), provide the output of intensity versus wavelength for the two polarized fluorescence components, thus enabling polarization or anisotropy to be established as a function of wavelength for the fluorescence. Highly polarized fluorescence spectral components indicate viscous fluorophores as would characterize heavy oil residues.

Figure 3:
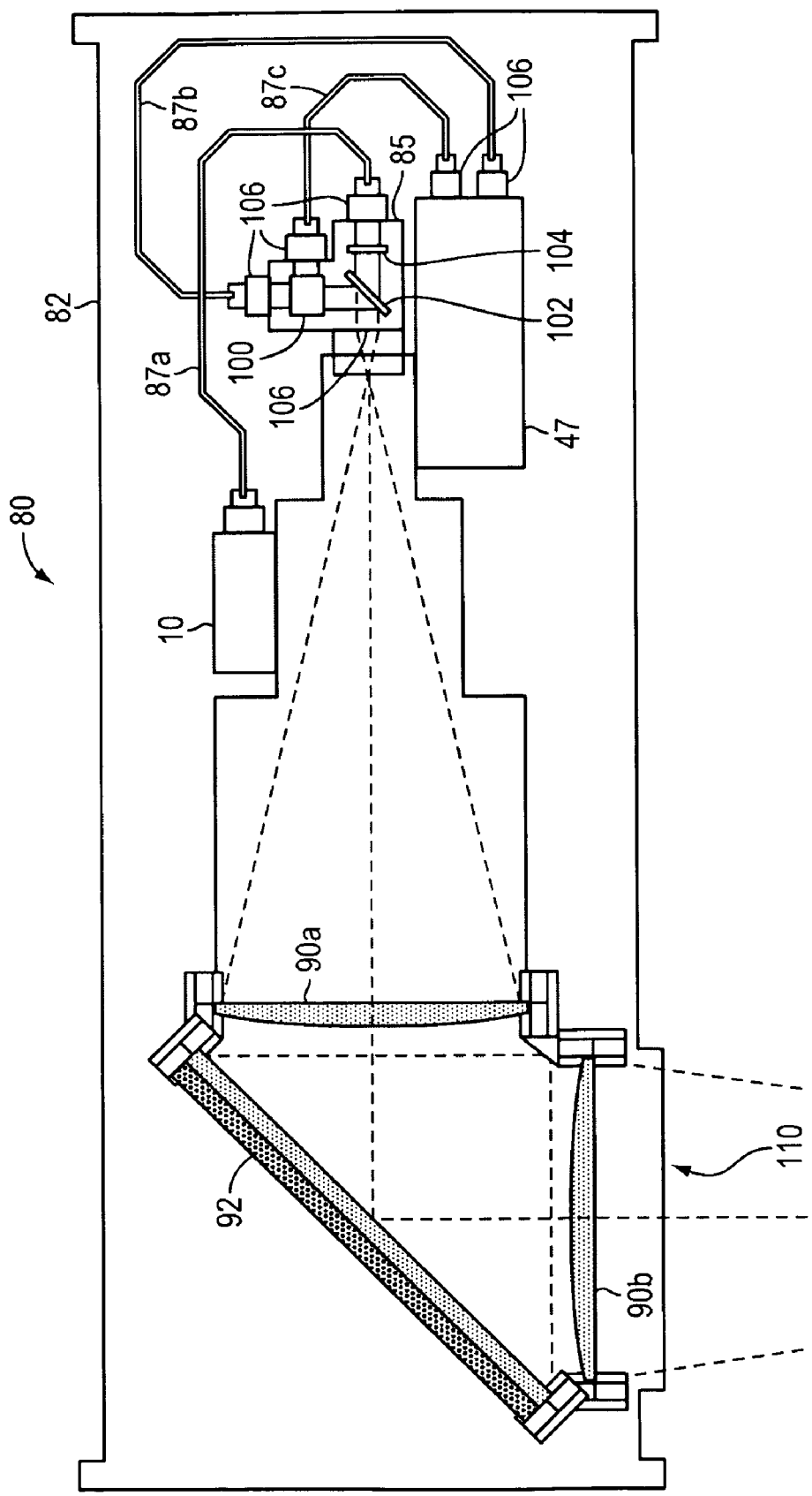
FIG. 3 schematically illustrates a fluorescence polarization module suitable for placement in an autonomous underwater vehicle (AUV) or a tethered remotely operated vehicle (ROV).

FIG. 3 shows an implementation 80 in which all of the optical components are assembled to fit into a small cylindrical housing or other enclosure 82 that can easily be incorporated into the body of a mobile underwater deployment platform such as an AUV or ROV. The main components of the instrument 80 are the fluorescence polarization module 85; a small laser source (e.g., a diode or diode-pumped solid state laser) 10; a miniature spectrograph 47 with an array detector such as a CCD (and, desirably, an embedded computer); fiber optic couplings 87a, 87b, 87c between the laser 10, module 85 and spectrograph 47; and a pair of lenses 90a, 90b and a folding mirror 92 to project the excitation laser source and collect the fluorescence. Polarization module 85 includes a polarizing cube 100, a dichroic filter 102, a polarizer 104, and lenses 106; these components operate as described above in connection with FIG. 1.

The instrument 80 has a side-viewing viewport window 110 so that when mounted in an AUV, the optical window 110 will face downward toward the sea floor. An autonomous data-acquisition software program resides in the embedded computer, and this program acquires FP spectra, geo-references each FP spectrum from navigational data from the deployment platform or a global positioning system (GPS) which may also be embedded in spectrograph 47, analyzes the data, and stores the data in local memory. The data-acquisition software can be configured so that it is remotely triggered by another computer (e.g., the deployment platform or on-board ship computer) or can be programmed to start and stop data acquisition once the deployment platform reaches certain preset coordinates. Additional optical elements may be introduced into the system to permit operation in a beam-scanning mode for imaging applications. Since heavy oils emit strong fluorescence signals, fluorescence polarization measurements can be acquired in the millisecond to second range for operation in real-time or near-real-time modes.

FP data acquisition and processing can be programmed to occur in a rapid timeframe consistent with the overall intensity of the FP signals and the sensitivity of the detectors. The programming can utilize computer algorithms, e.g., to identify fluorescence that shows significant polarization; storing and reporting records relating only to fluorescence polarizations above a threshold prevents the system from becoming overloaded with null data files. The computer may include a database of spectra as described above and the programming may include routines for querying the database and making comparisons among spectra for identification purposes.

Instruments as described herein and other configurations containing components assembled to excite fluorescence from a sample and to determine the degree of fluorescence polarization may be used for other applications involving differentiatiion of viscous oils from other fluorophores. For example, FP may be used to monitor the cleanup of oil spills by analyzing the contents of liquid in the pipeline used to draw the spillage region from the aquifer into a holding tank. Fluorescence polarization probes also may be used in borehole measurements to determine the presence of heavy oils in an oil exploration activity, either in terrestrial or underwater drilling. The same technique may be used in connection with ground-penetrating assemblies such as cone penetrometers for locating polluting viscous oil residues in the soil or groundwater.

The instruments and methods described herein may be used to monitor viscosity changes in fluorescent materials. For example, the curing of composites, paints and coatings containing a fluorescent chromophore may be expected to be accompanied by an increase in fluorescence polarization as the curing proceeds. The approach of the present invention may therefore be used to remotely monitor paint drying, for example, or as a viscometer for fluids such as oils containing a fluorophore.

EXAMPLES

Example 1

Laboratory Tests. A laboratory setup suitable for measuring the fluorescence polarization spectra of various test samples was constructed. The excitation source was a 473 nm diode-pumped solid-state laser. The laser output was collimated by a 25 mm diameter f2 lens, transmitted through a linear polarizer oriented vertically, transmitted through a 45° dichroic filter, and then focused by a 25 mm diameter f2 lens onto the sample. The fluorescence emission from the sample was collected and collimated by the same lens, reflected off the dichroic filter at 90°, transmitted through a variable polarizer, and then focused by a 25 mm diameter f2 lens onto a 200-micron core optical fiber. The distal end of the optical fiber was coupled to a spectrograph that disperses the fluorescence signal into discrete wavelengths that are detected with a CCD detector. The vertical and horizontal fluorescence polarization spectra were recorded sequentially by manually rotating the variable polarizer into its vertical and horizontal polarization orientation.

Figure 4B:
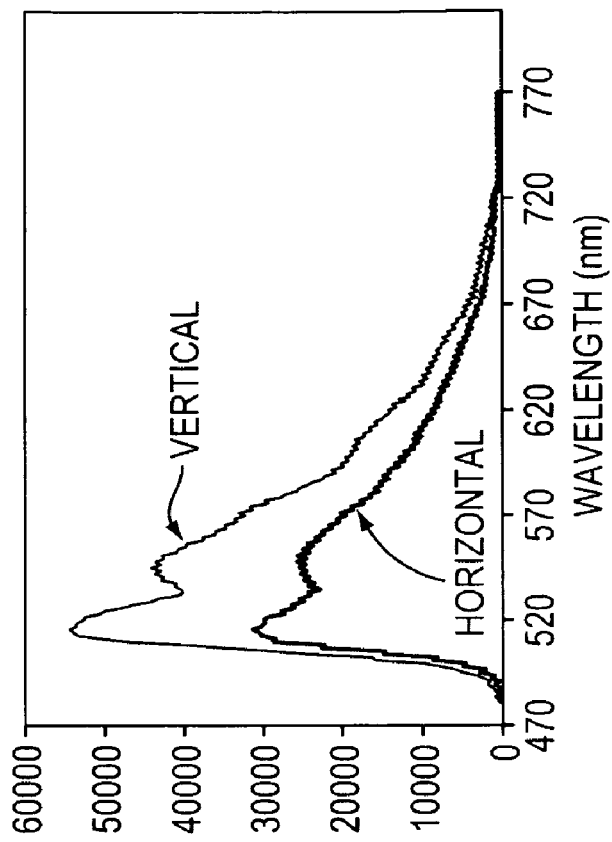
FIGS. 4A and 4B graphically depict fluorescence polarization spectra of gasoline and residual oil.
Figure 4A:
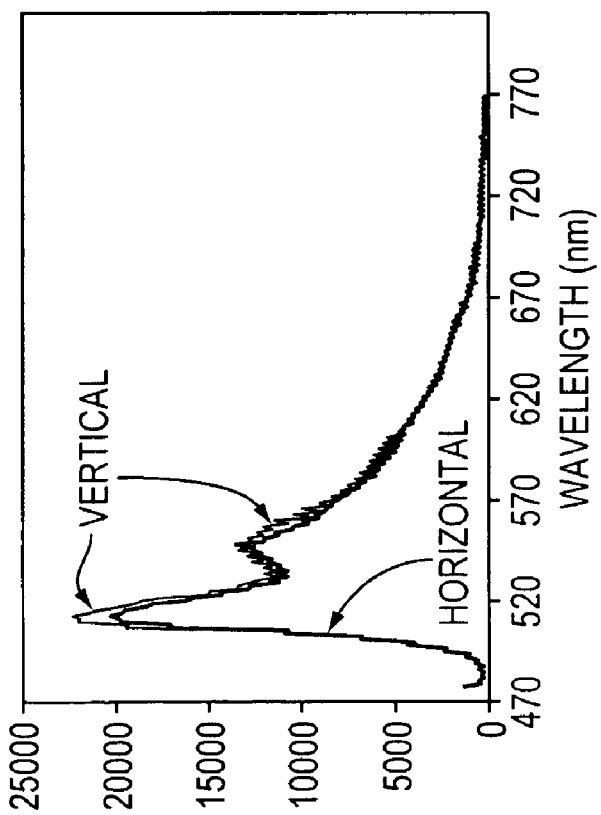

FIG. 4 compares the vertical and horizontal fluorescence polarization spectra of gasoline and a group V residual oil sample that were obtained using this apparatus. These two samples have different viscosities, since gasoline is a non-viscous liquid while the residual oil has high liquid viscosity. With gasoline, FIG. 4 shows that there is no difference in the intensity of the horizontal and vertical fluorescence polarization spectra. Conversely, FIG. 4 shows that there is a significant difference in the intensity of the two polarization components of the fluorescence spectra of heavy oil. These results show that fluorescence polarization can be used to distinguish heavy oils, which are very viscous types of petroleum products, from other fluorophores that may be present in water such as light aromatic hydrocarbons or organic vegetative matter.

To further illustrate the selectivity of FP, spectra of marine vegetation samples (seaweed and algae-covered rock) contaminated with a thin layer of residual heavy oil were obtained. With these samples, chlorophyll fluorescence is observed with the 473 nm excitation. However, chlorophyll does not exhibit fluorescence polarization since the chloroplast thylakoid membrane where the chlorophyll is found is very fluid. The fluidity of biological membranes is determined mainly by the length and the degree of saturation of alkyl chains in fatty acids of the constituent lipids. Thylakoid membranes of plants contain galactolipids with highly unsaturated fatty acids and a small portion of phospho- and sulfolipids. Thus, a relatively low viscosity is expected for the thylakoid membrane.

Figure 5:
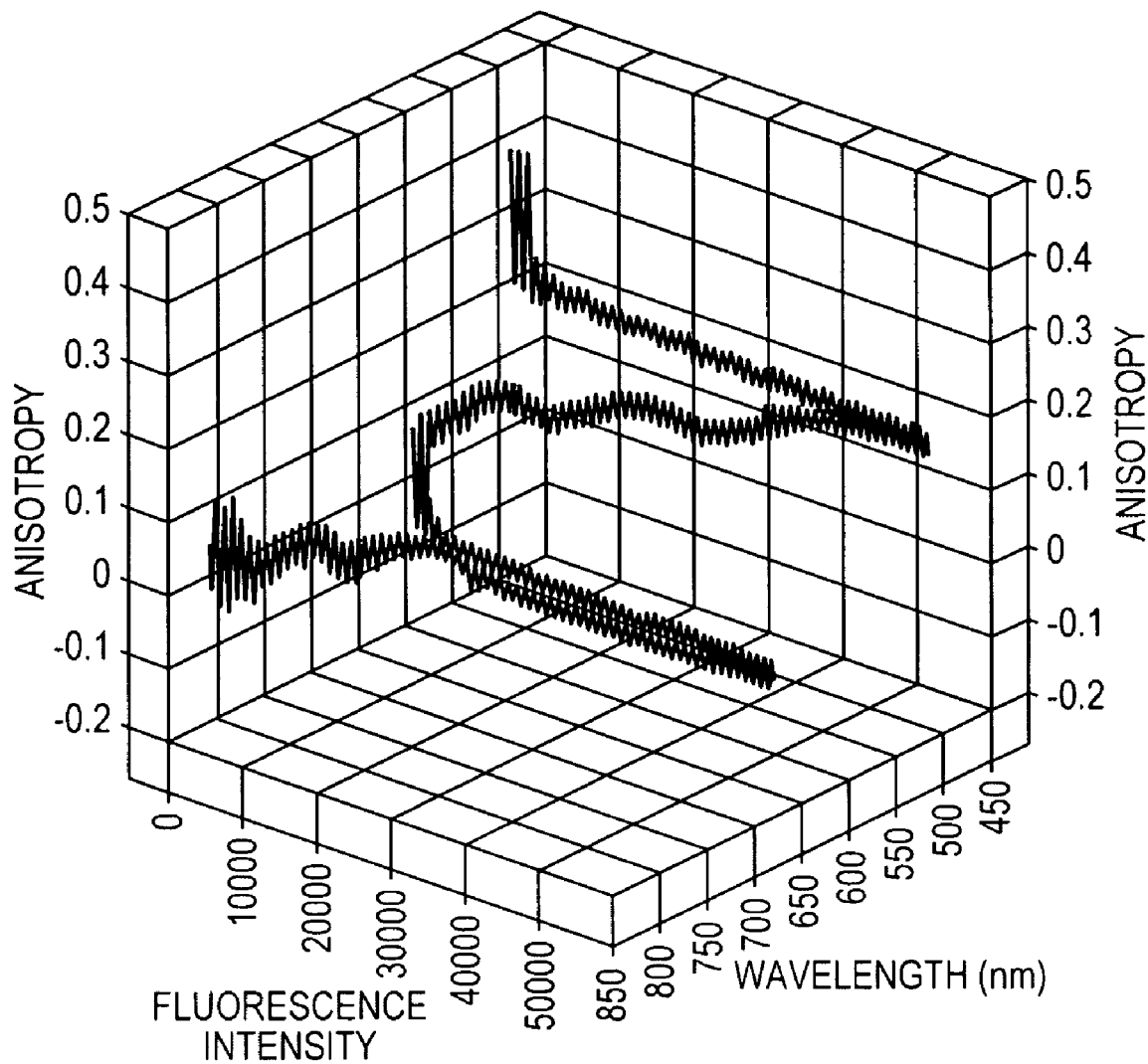
FIG. 5 is a 3D plot of fluorescence intensity, anisotropy, and wavelength for residual oil contaminated seaweed (left) and moss-covered rock (right).

FIG. 5 shows the three-dimensional plot of the fluorescence intensity (vertical), fluorescence anisotropy, and wavelength of the rock and seaweed. The residual oil fluorescence (520 nm peak) shows a high anisotropy value (0.15), while the chlorophyll fluorescence (680 nm peak) shows no anisotropy. This demonstrates that heavy oil can easily be differentiated from marine fluorescence backgrounds by means of fluorescence polarization value. Thus, fluorescence polarization increases the reliability of detecting heavy oils with the fluorescence technique.

Figure 6A:
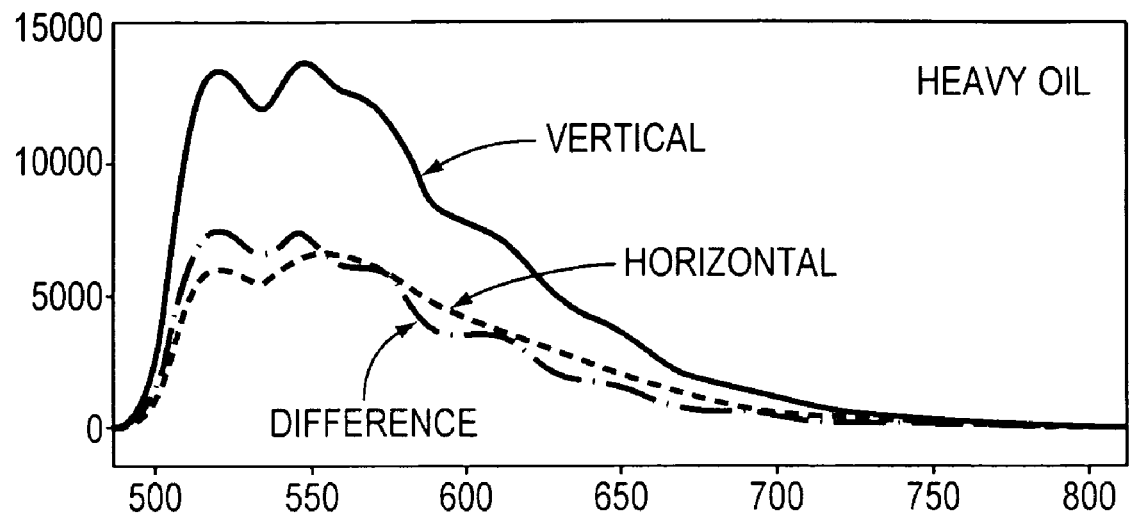
FIGS. 6A and 6B graphically depict fluorescence polarization spectra of heavy oil and ambient light, respectively.
Figure 6B:
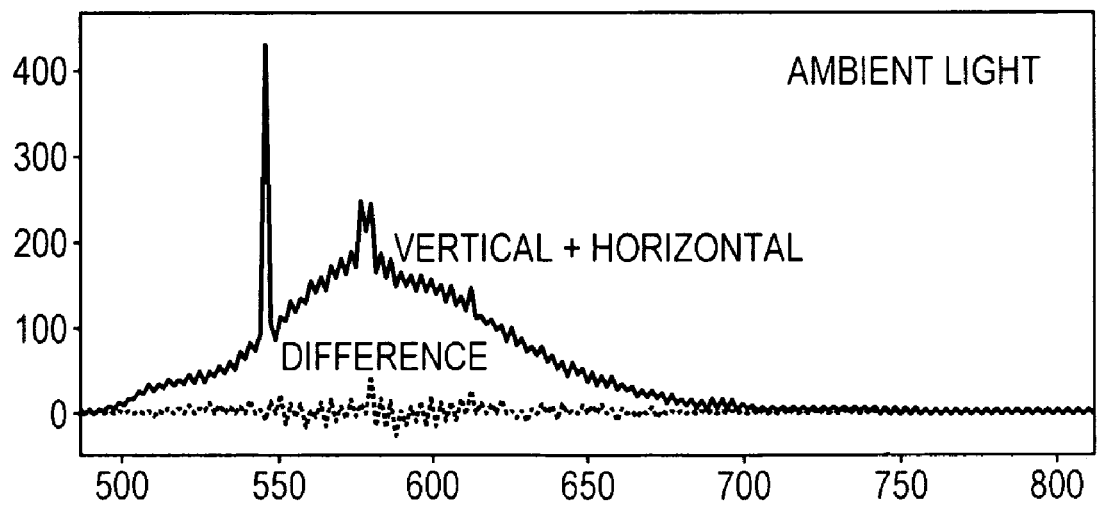

FIG. 6 illustrates the vertical, horizontal and difference (polarization) fluorescence spectrum of a heavy oil sample. Also shown is the vertical, horizontal and difference spectrum of ambient light. The ambient light difference spectrum is null, since ambient light is unpolarized. Thus, ambient light will not show up in the difference fluorescence spectrum of heavy oil. This result illustrates the utility of the FP technique in making daylight measurements of heavy oil residues in solar illuminated aquifers, thus avoiding expensive pulsed laser sources and time-gated detectors.

Example 2

Field Tests. For field testing, a fluorescence polarization probe of configuration similar to that illustrated in FIG. 1 was mounted in a waterproof enclosure. The main components of the probe were a fiber-optic fluorescence polarizer and a telescopic focusing/collection optic. The fiber-optic fluorescence polarizer utilized three miniature optical trains (laser excitation, perpendicular FP collection, and parallel FP collection) arranged in a backscattering light-collection probe configuration. The probe telescope was a simple refractor telescope having a 50 mm diameter, 100 mm focal length objective lens and a 9 mm diameter, 11 mm focal length eyepiece. The telescope was used to focus the laser beam onto the sample and also to collect the fluorescence emitted by the sample. With the telescope as the front optical component of the fluorescence polarization probe, the probe in this example can detect fluorescence signals from fluorescent samples less than one meter to several meters away. The telescope focus may be adjusted by moving the eyepiece manually between the polarizer and the objective lens. However, the eyepiece can be mounted into a linear actuator, and the linear movement can be controlled via software to provide active focusing of the FP probe.

The FP probe instrumentation included an excitation source, photomultiplier detectors, and a data-acquisition module. The excitation source was a 100 mW, 532 nm diode-pump solid-state laser from AIXIZ. Detection of the two fluorescence polarization components was performed using two fiber-optically coupled photomultiplier tubes (PMT) each incorporating a bandpass filter (40 nm bandwidth) centered at 585 nm. Data acquisition was performed with a LabJack (LabJack U3) data-acquisition board (DAQ) coupled to a laptop computer via a USB cable. The DAQ was programmed to record and display both the raw fluorescence signals from the two PMT channels and also to calculate and display the polarization values. The programming also allowed a GPS signal to be recorded along with the FP signals to facilitate georeferencing of FP data. The programming allowed the data-acquisition time of the PMT channels to be changed, balanced the response of the two signals from the two emission legs of the FP probe, and obtained the bias of the two PMTs. Such programming is straightforwardly realized without undue experimentation.

The ability of the instrument to detect heavy oil residues was assessed at The National Oil Spill Response Test Facility (OHMSETT). OHMSETT's above-ground concrete test tank measures 203 meters long by 20 meters wide by 3.4 meters deep. The tank is filled with 2.6 million gallons of clear saltwater. The tank also incorporates a main towing bridge capable of towing test equipment at speeds up to 6.5 knots. During testing of the FP probe in the test tank at OHMSETT, the FP probe was suspended from the towing bridge, with the probe partially submerged in the tank. The FP probe waterproof housing was attached to one end of a 6' long aluminum extension rod, which allowed adjustable positioning of the probe at a desired distance from the oil test platform. The extension rod was then attached to a metal flange that bolted to the bottom of the bridge towbar. In addition, a GPS antenna for georeferencing was mounted on a short crossbar attached to the top end of the extension rod, positioning the GPS above water during testing. The FP probe was connected to the laser and detector modules, which were located inside the towing bridge controller room, by 25-meter-long optical fiber cables. The GPS antenna was connected to the roaming GPS receiver, also located inside the bridge controller room, by a 20-foot-long coaxial cable. The beacon GPS receiver and antenna were located on the walkway along the side of the test tank.

Two test pallets containing different types of heavy oil residues (Sundex, #6 Oil, and Asphalt) as well as blanks were placed on the bottom of the test tank. The two pallets were arranged end to end with about 5 feet separation between them. Before testing was started, the FP probe distance to the test pallet surface was adjusted so that it was approximately at the probe laser-beam focus (~2 meters). This was accomplished by adjusting the probe extension rod.

Grid scans of the probe laser over the test pallets containing the oil targets were carried out. The orientation of the test pallets was along a south-to-north direction. Grid scans were started just east of the pallets so that the first line was about 2 feet away from their edge. The tow bridge was moved from south to north, and at the end of each line the probe was translated by about 6 inches. The last line was also about 2 feet away from the other edge of the pallets. The tow speed was kept constant during each scan. Strong fluorescence polarization peaks were observed whenever the laser output struck one of the oil targets on the test pallet.

Figure 7:
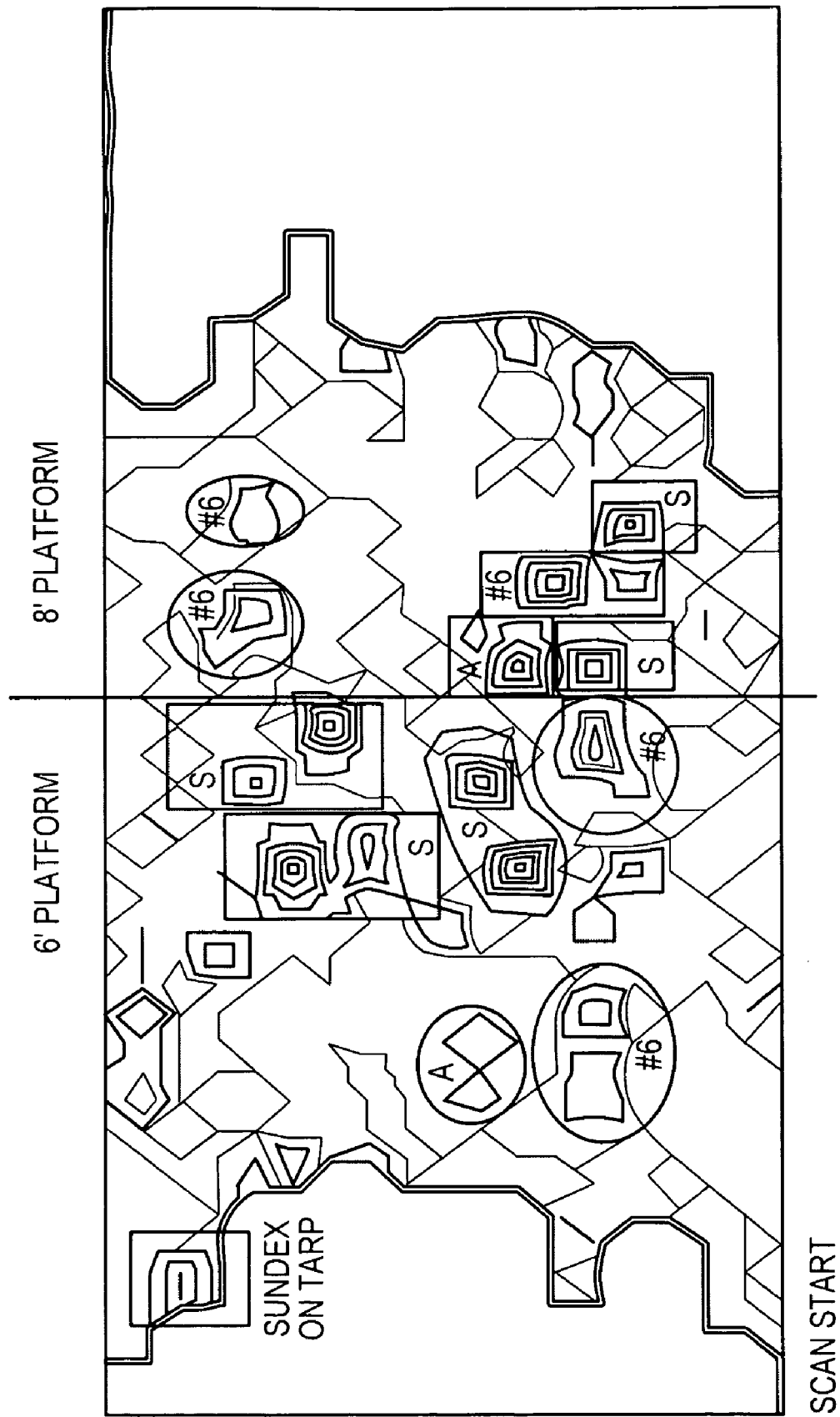
FIG. 7 is a contour map of fluorescence polarization intensity as a function of GPS position obtained in test of fluorescence polarization detector for heavy oil locations in the OHMSETT test tank.

During the grid-scan acquisitions, GPS signals were recorded along with the FP signals. This facilitated the construction of maps of the FP intensity. FIG. 7 shows the grid map for the 1-knot-speed grid-scan fluorescence polarization data. The FP signals that were detected, which indicated the presence of heavy oil, were situated mainly in the center of the grid box where the pallets containing the oil targets were located. (In the figure, #6 refers to #6 oil; S refers to Sundex; and A refers to asphalt).

It was determined during testing of the FP probe in the OHMSETT tank that the tank paint exhibits intense fluorescence. However, the fluorescence polarization value of the paint was observed to be quite small. As a result, the grid scans in FIG. 7 did not show this background. Detecting the heavy oil with conventional nonpolarized fluorescence techniques, as suggested in prior art, would thus fail in this situation, since the signal would be washed out by this background. Similarly, the fluorescence polarization measurements were insensitive to ambient daylight. This indicates that fluorescence polarization provides selectivity for heavy oil detection against interference from other nonpolarized fluorophores and that it can be used during daylight operations.

As noted above, the approach of the present invention is applicable to detection of heavy oil with high viscosity, and particularly for locating subsurface spills or deposits of such materials, but also useful for detecting floating slicks of viscous oils. However, the invention is broadly applicable to other uses, such as detection of Raman scattering (which frequently accompanies fluorescence). If the fluorescence is unpolarized while the Raman is polarized, then the Raman or fluorescence may be separated from each other by spectral subtraction. Similarly, Raman is a relatively weak phenomenon, but it generally does exhibit polarization. Interference from ambient light is common in Raman spectroscopy. However, ambient light is removed from the Raman spectrum in the Raman polarization spectrum.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. Apparatus for detecting the presence of oil in an aqueous environment, the apparatus comprising:
    a) source of polarized fluorescence excitation light;
    b) a collector for collecting fluorescence from a target region to which the source is directed;
    c) a separator for separating vertically and horizontally polarized components of the collected fluorescence; and
    d) an analysis module for determining the presence of oil based on intensities of the vertically and horizontally polarized components.

2. The apparatus of claim 1 further comprising an optical detector for measuring the intensities of the vertically and horizontally polarized components.

3. The apparatus of claim 2 wherein the detector includes at least one optical filter to separate the collected fluorescence from the excitation light.

4. The apparatus of claim 2 wherein the detector comprises means for recording the intensities of the vertically and horizontally polarized components as spectra.

5. The apparatus of claim 1 further comprising a light shield for preventing interference from ambient sunlight.

6. The apparatus of claim 1 wherein the source and collector are physically separate from, but communicate with, the separator and the analysis module.

7. The apparatus of claim 1 further comprising an imaging module for providing an image of detected oil.

8. The apparatus of claim 1 further comprising a mapping module for providing a geographic map of detected oil.

9. A method of detecting the presence of oil in an aqueous environment, the method comprising the steps of:
    a) directing polarized fluorescence excitation light at a target region;
    b) collecting fluorescence from the target region;
    c) separating vertically and horizontally polarized components of the collected fluorescence; and
    d) determining the presence of oil based on intensities of the vertically and horizontally polarized components.

10. The method of claim 9 further comprising measuring the intensities of the vertically and horizontally polarized components.

11. The method of claim 10 further comprising the step of separating the collected fluorescence from the excitation light.

12. The method of claim 10 further comprising the step of recording the intensities of the vertically and horizontally polarized components as spectra.

13. The method of claim 12 further comprising the step of identifying fluorescing species by comparing the spectra to a database of known fluorophores.

14. The method of claim 10 further comprising the step of preventing interference from ambient sunlight.

15. The method of claim 10 further comprising the step of generating an image of detected oil.

16. The method of claim 10 further comprising the step of generating a geographic map of detected oil.

17. The method of claim 10 further comprising the step of scanning a wide area to identify an area of suspicion corresponding to the target region.

* * * * *